(12) United States Patent
Linares

(10) Patent No.: US 8,211,185 B2
(45) Date of Patent: Jul. 3, 2012

(54) COMPOSITE JOINT IMPLANT INCORPORATING INNER EXTENDING STEM WITH OUTWARDLY DISPLACEABLE BRANCHES FOR SECURING TO A SECTIONED BONE END

(75) Inventor: Miguel A. Linares, Bloomfield Hills, MI (US)

(73) Assignee: Linares Medical Devices, LLC, Auburn Hills, MI (US)

( * ) Notice: Subject to any disclaimer, the term of this patent is extended or adjusted under 35 U.S.C. 154(b) by 279 days.

(21) Appl. No.: 12/666,110

(22) PCT Filed: May 1, 2009

(86) PCT No.: PCT/US2009/042510
§ 371 (c)(1),
(2), (4) Date: Dec. 22, 2009

(87) PCT Pub. No.: WO2009/111805
PCT Pub. Date: Sep. 11, 2009

(65) Prior Publication Data
US 2011/0035022 A1    Feb. 10, 2011

Related U.S. Application Data

(60) Provisional application No. 61/033,954, filed on Mar. 5, 2008.

(51) Int. Cl.
*A61F 2/30* (2006.01)

(52) U.S. Cl. .................. 623/23.44; 623/23.12
(58) Field of Classification Search ............... 623/16.11, 623/18.11, 23.12–23.14, 23.23–23.27, 23.33, 623/23.44, 23.47; 606/63, 68
See application file for complete search history.

(56) References Cited

U.S. PATENT DOCUMENTS

| | | | | |
|---|---|---|---|---|
| 2,685,877 A | * | 8/1954 | Dobelle | 623/23.11 |
| 5,729,205 A | | 3/1998 | Kwon | |
| 6,962,607 B2 | | 11/2005 | Gundlapalli et al. | |
| 2005/0256585 A1 | * | 11/2005 | Park et al. | 623/23.14 |
| 2007/0219638 A1 | * | 9/2007 | Jones et al. | 623/19.11 |

FOREIGN PATENT DOCUMENTS

| | | |
|---|---|---|
| KR | 10-20010087178 | 9/2001 |
| KR | 10-0421161 | 4/2005 |

* cited by examiner

*Primary Examiner* — Brian Pellegrino
*Assistant Examiner* — Megan Wolf
(74) *Attorney, Agent, or Firm* — Gifford, Krass, Sprinkle, Anderson & Citkowski, P.C.

(57) ABSTRACT

An artificial joint implant in use with a bone and including a three dimensional shaped body have an exterior configured and joint defining face. An annular shaped recess is formed within a seating location of the implant for securing the body over a sectioned end of the bone. A stem extends from the body inwardly within the bone and exhibits at least one support for engaging an inner bone surface and in order to maintain the implant in secured fashion to the bone.

10 Claims, 3 Drawing Sheets

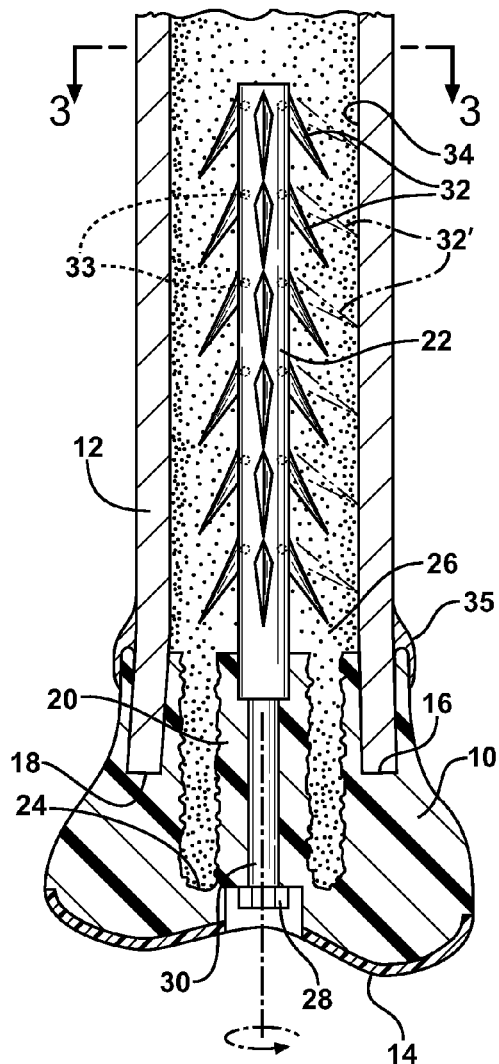
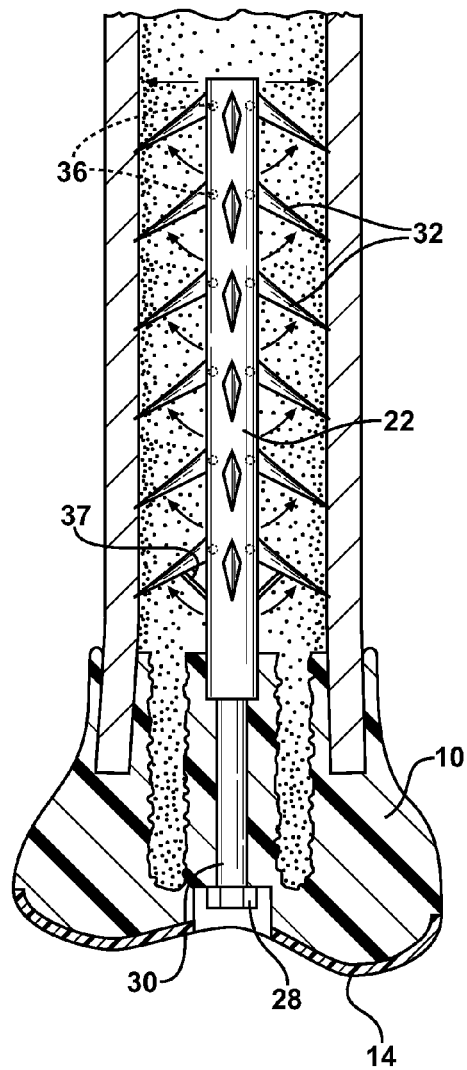
FIG. 1      FIG. 2
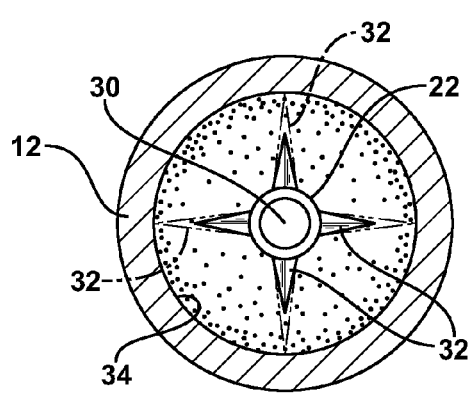
FIG. 3

__US 8,211,185 B2__

COMPOSITE JOINT IMPLANT INCORPORATING INNER EXTENDING STEM WITH OUTWARDLY DISPLACEABLE BRANCHES FOR SECURING TO A SECTIONED BONE END

CROSS-REFERENCE TO RELATED APPLICATIONS

The present application claims the priority of U.S. Provisional Patent Application Ser. No. 61/033,954, filed Mar. 5, 2008, and entitled Composite Joint Implant Incorporating Inner Bone Extending Stem with Outwardly Displaceable Branches for Securing to a Sectioned Bone End.

FIELD OF THE INVENTION

The present invention relates to a composite implant secured to a retrofitted end of a conventional joint defining bone. More specifically, the present invention teaches a combination end secured joint implant and inwardly extending and supporting stem for providing both end support and adjustment of the implant, as well as assisting in providing even distribution of associated bone marrow within the interior of the bone.

BACKGROUND OF THE INVENTION

The prior art is documented with varying types of bone implant and/or joint assemblies. More recent technological advances focus on the viability of securing an artificial joint to an existing bone. A problem associated with undertaking such implants is the tendency of the artificial joint to detach or otherwise misalign relative to the bone to which is secured.

SUMMARY OF THE PRESENT INVENTION

An artificial joint implant in use with a bone and including a three dimensional shaped body have an exterior configured and joint defining face. An annular shaped recess is formed within a seating location of the implant for securing the body over a sectioned end of the bone. A stem extends from the body inwardly within the bone and exhibits at least one support for engaging an inner bone surface and in order to maintain the implant in secured fashion to the bone.

Additional features include the support exhibiting a plurality of outwardly displaceable branches, a clip further associated with each of the branches. A turn screw is also located at the joint defining face and interconnects, via an internal rotatable shaft, with the support. In another variant, a rotatable threaded shaft is operable, via an end face mounted turn screw, for actuating the at least one support in an outward fashion.

In another variant, the support includes a rotatable wing nut portion or, alternatively, at least one aperture. A soft plastic lubricated surface can be applied, or otherwise coated, to the exterior configured and joint defining face. The implant may also exhibit a composite hard plastic material.

BRIEF DESCRIPTION OF THE DRAWINGS

Reference will now be made to the attached drawings, when read in combination with the following detailed description, wherein like reference numerals refer to like parts throughout the several views, and in which:

FIG. 1 is a first illustration of a composite joint implant in cutaway and showing the composite end portion positioned in place, with the inner bone extending stem pre-positioned with associated branches in first retracted positions;

FIG. 2 is a succeeding illustration to that shown in FIG. 1, and in which the stem supported branches are outwardly displaced into frictional engagement with inner wall positions of the associated bone via the assistance of outwardly biasing spring clips;

FIG. 3 is a sectional view taken along line 3-3 of FIG. 1 and illustrating a top view of the interiorly extending stem with outwardly displaced frictional locating and supporting branches;

DETAILED DESCRIPTION OF THE PREFERRED EMBODIMENTS

Figure 4:
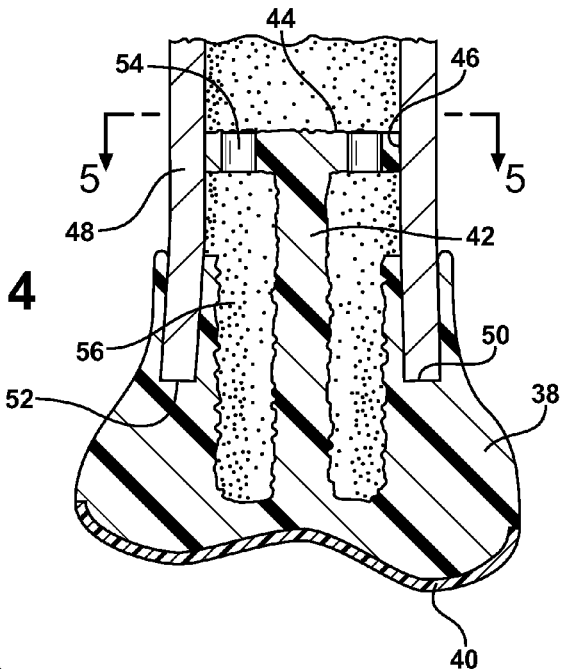
FIG. 4 is a side cutaway illustration of a further embodiment in which the inner stem is reconfigured to exhibit an innermost mounted and marrow passageway defining support abutting an inner perimeter of the associated bone.

Referring now to FIG. 1, a first illustration is shown of a composite joint implant 10 in cutaway and which is mounted to a sectioned end of a patient's bone 12. The implant 10 is constructed of a suitable material and which can include, among other things, a composite plastic, metal or combination thereof, in addition to additional materials. The implant 10 is further configured, such as is shown, so that it mimics a joint defining end face (not limited to any of a knee, elbow, hip, ankle, writs or the like), over an exposed face of which is covered or otherwise applied a composite soft plastic surface layer 14, such further corresponding to a substantially frictionless wear and cartilage supporting layer.

As further illustrated in cutaway, the implant 10 exhibits a three dimensional configuration with an inner facing and generally perimeter extending recessed rim, see as shown at 16 and which is sized and configured so that it annularly seats a mating sectioned edge profile, at 18, of the associated bone 12. The use of cements or other adhesives is contemplated in establishing at least an initial bond between the implant 10 and the bone 12. Although not shown, an additional bone and end-secured implant can be provided in opposing and joint defining fashion with respect to that illustrated. Alternatively, a synthetic (e.g. plastic) bone can be substituted for a second natural bone, and in order to establish any desired joint arrangement.

The sectioned inner configuration of the composite implant 10 is further such that it defines a central and interiorly extending and stem supporting structure, as shown at 20, for supporting thereupon in continued interior extending fashion an inwardly projecting stem 22. The implant further configures an annular valley defined between the outer perimeter side and the inner central support structure 20, see recessed surface 24, this providing additional surface area for an interior volume of bone marrow 26 associated with the bone 12 to create new bone which bonds to the abutting locations of the end secured implant 10, concurrent with the marrow establishing additional bonds with the annular rim 16 and adjoining bone edge 18.

Referring again to FIG. 1, the stem 22 extends inwardly from the inner supporting structure 20 associated with the implant 10. A turn screw (such as shown but not limited to a hex head nut) is indicated at 28 situated at a recessed (non wearing) surface of the exposed implant end face, and which is rotatably slaved with a shaft 30 in turn extending through an interior of the support structure 20 and engaging the connected stem 22.

A plurality of individual branches are shown in solid at 32 in a retracted position in pivotally supported and connecting fashion relative to the peripheral and linear extending surfaces of the stem 22. The stem 22 and pivotally secured branches 32 are preferably constructed of a likewise metal/plastic composite, although other material considerations can come into play in selecting an appropriate stem and branch construction. Although not clearly shown, the branches 32 are hingedly or pivotally secured to extending locations of the stem 22 (see pivotal linkage connections 33 with selected branches 32 in FIG. 1) and are further interconnected, through appropriate linkages, with the rotatable shaft 30 and so that, upon rotating the hex nut 28 in a selected direction, the branches pivot outwardly to further positions shown at 32' and at which they frictionally engage against inner facing wall surfaces, at 34, of the associated bone 12. Along these lines, it is contemplated and understood that any suitable mechanical connection can be provided for converting a rotary input applied to an interior of the stem (such as to a continuation of the rotating shaft 30 extending in a journalled or coaxial fashion within a hollow interior (not shown) of the stem, and further in order to coact with each of the pivotal linkage connections 33 and to in turn cause the individual associated branches to outwardly deflect in the manner shown to the bone inner wall engaging locations.

In this fashion, and upon the projecting edges of each individual branch engaging a selected inner bone surface location, the composite and end supported implant 10 is sufficiently anchored in place and prevented from unseating from its securing location to the bone 12, such as prior to the originally applied adhesive having an opportunity to more evenly bond and/or through the action of the bone regenerating marrow and external bone growth in the region surrounding the implant to bone mounting (see such bone growth as representatively shown at 35 in FIG. 1). An additional advantage associated with the stem locking arrangement is in preventing bone marrow from escaping from the implant to bone connection, and by virtue of the screw tightening resulting in the implant being drawn in a seal-tight fashion against the sectioned edge 18 of the bone. A secondary advantage associated with the inner stem and multiple branch arrangement is in assisting in maintaining an even distribution of marrow throughout the length of the bone interior.

Referring now to FIG. 2, a succeeding illustration is shown of a substantially related embodiment and in which the stem supported branches 32 are outwardly displaced into frictional and fixed engagement with inner wall positions of the associated bone via the assistance of outwardly biasing spring clips, see as further shown at 36 and which are provided in addition and/or substitution to the pivotal linkage connections 33 in FIG. 1. The clips 36 are configured such that, upon rotating the hex head 28 a selected range, the outward actuation of the branches 32 causes optionally provided springs (see at 37) to engage between the branches and the associated stem locations to maintain the branches in outwardly displaced and biasing condition in which they frictionally contact the associated inner wall locations of the associated bone. FIG. 3 is a sectional view taken along line 3-3 of FIG. 1 and illustrating a top view of the interiorly extending stem with outwardly displaced frictional locating and supporting branches, and such as which can be secured through either the clips 36 or frictional bias of the pointed ends associated with the branches in contacting locations with the inner wall surface of the bone.

Referring now to FIG. 4, a side cutaway illustration is shown at 38 of a further embodiment of composite implant, this again including a soft plastic lubricating surface wearing or cartilage layer 40. An associated inner stem 42 is reconfigured to exhibit an innermost mounted and marrow passageway permitting and defining support 44, which in turn is dimensioned so as to abut an inner perimeter defining surface 46 of an associated bone 48, such as to which the implant 38 is secured. In the embodiment illustrated, the stem 42 can also be integrally formed with the end established implant body, and such that the support 44 is dimensioned to contact the inside surfaces of the bone wall in frictionally contacting fashion and without the requirement of any degree of post insertion actuation such as associated with the stem and branch arrangement in FIG. 1. The implant 38 is again configured such that an inner recessed and annular rim 50 is configured so that it seats over a sectioned end 52 of the bone 48 to which the implant is attached (such as is again assisted through the use of glues or adhesives). It is also understood that the implant 38 can be cemented or otherwise permanently secured to the bone 48, such as though the provision of such an adhesive alone along the annular rim 50 connection to the bone (again at 52).

Figure 5:
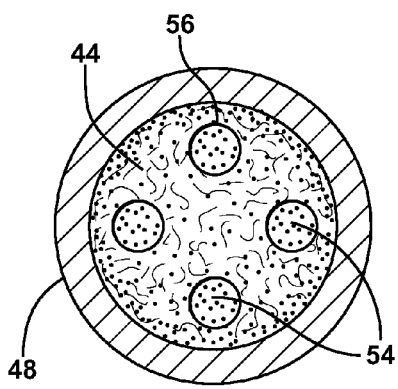
FIG. 5 is a cutaway view taken along line 5-5 of FIG. 4 and better illustrating the passageways defined in the support for facilitating marrow passage between first and second sides of the disc.

FIG. 5 is a cutaway view taken along line 5-5 of FIG. 4 and better illustrating passageways 54 defined in the support for facilitating marrow passage between first and second sides of the disc support 44. The passageways 54 are provided so that the natural marrow inside of the bone, at 56, can pass between both sides of the support 44 and thereby remain evenly distributed along the interior of the bone.

Figure 6:
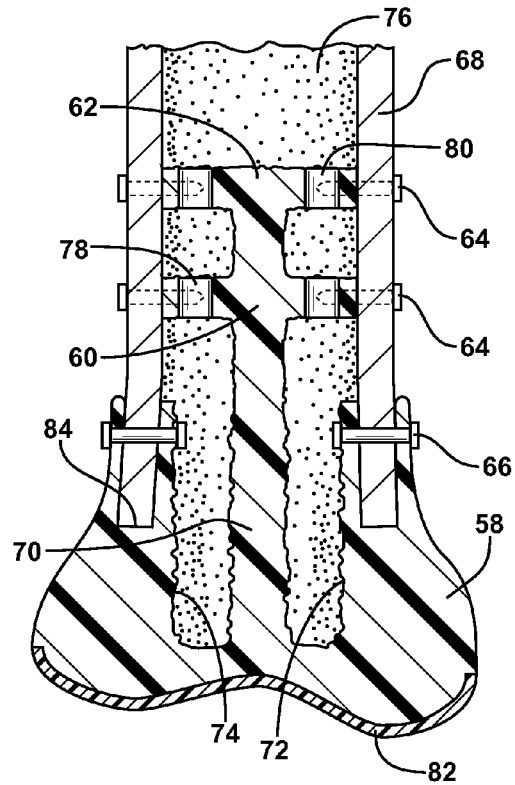
FIG. 6 is a side cutaway view of further modified variant of the embodiment in FIG. 4, and in which first and second supports are arranged in spaced fashion and, in combination with the end implant, can be pin secured to locations associated with the bone.

Referring now to FIG. 6, a side cutaway view is shown of a further modified variant of the embodiment in FIG. 4, and in which an implant 58 includes first 60 and second 62 widthwise extending supports arranged in spaced fashion and, in combination with the end implant 58, can be secured by such as a pin, see at 64 and 66, to locations associated with a bone 68. An inner extending stem portion is again shown at 70 and between this and the outer annular profile of the implant 58 an undercut surface is configured (see at 72 and 74) for facilitating the growth and inter-adherence of new bone associated with the inner marrow 76.

As in earlier embodiments, the inner bone supports 60 and 62 each include through holes, see at 78 and 80, for facilitating lengthwise interior communication of marrow 76. The implant otherwise is similar to those previously disclosed and again includes a lubricated, substantially frictionless and wear supporting end exposed surface 82 and appropriate annular end recess and undercut engagement, at 84, of the implant 58 for secure and correctly aligned mounting to the sectioned end of the natural bone 68.

Figure 7:
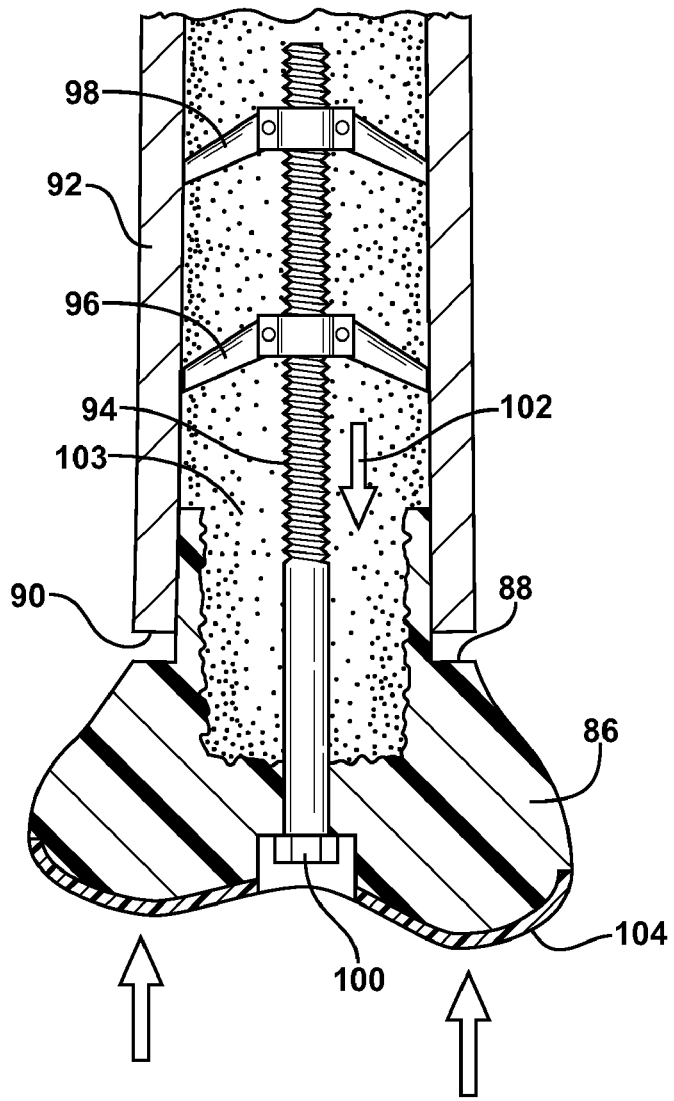
FIG. 7 is a side cutaway view of a further embodiment of cutaway joint implant and illustrating both an undercut arrangement for locating and supporting the implant in combination with an interiorly threaded stem for supporting a pair of modified and interior displaceable wing portions securing against inner perimeter locations of the associated bone.

Referring to FIG. 7, a side cutaway view is shown of a yet further embodiment 86 of a cutaway joint implant and illustrating both an undercut arrangement 88 (shown in a preseated fashion relative to the bone) and for locating and supporting the implant 86 to a sectioned end 90 of a bone 92, this in combination with an interiorly threaded stem 94 for supporting a pair of modified and interior displaceable wing portions 96 and 98 and for securing against inner perimeter locations of the associated bone 92. An end screw 100 (such as a hex screw which is again substantially recess mounted to a central location associated with the implant end surface) can be provided and to which the stem 94 is rotatably slaved. In this fashion, rotation of the screw 100 results in wing portions 96 and 98 being drawn in a linear direction 102 towards the end support implant 86, thereby adding an inwardly pulling bias of the implant undercut edge 88 against the end sectioned edge 90 of the bone, this again facilitating more complete bonding of the composite implant against the bone, as well as preventing loss of marrow 103.

Figure 8:
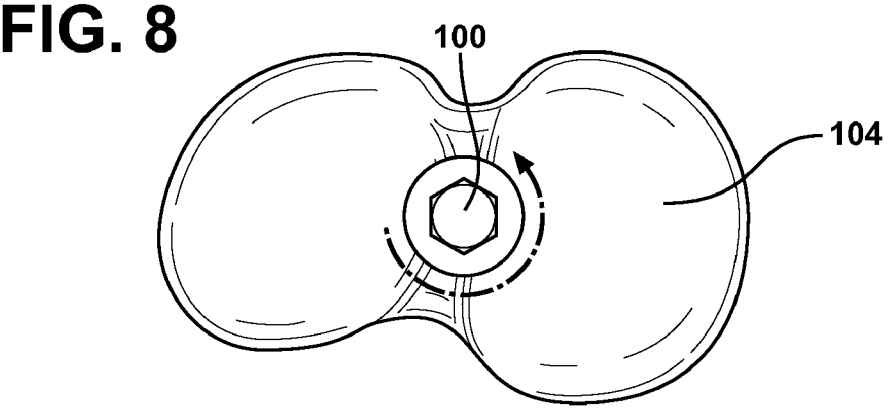
FIG. 8 is an end view of FIG. 7 and showing the end disposed hex head screw accessible from the joint and for facilitating inner linear displacement of the interiorly supported wing portions.

FIG. 8 is an end view of FIG. 7, and showing the end disposed hex head screw, accessible from the joint and rotatable as indicated for facilitating inner linear displacement of the interiorly supported wing portions (again at 96 and 98 in FIG. 7). A lubricated end wear surface 104 is again illustrated which is secured to an outer face surface of the implant 86, another opposing and joint defining bone and optional implant not shown but also being contemplated as completing the joint assembly and so that the opposing and proximately located (wear) surfaces collectively establish a joint zone. Although not shown, additional features such as ligaments, cartilage (either natural or synthetic) are understood to be incorporated into the joint assemblies as described herein.

Having described my invention, other and additional preferred embodiments will become apparent to those skilled in the art to which it pertains, and without deviating from the scope of the appended claims.

I claim:

1. An artificial joint implant adapted for use with a bone, said implant comprising:
    a three dimensional shaped body having an exposed joint defining face;
    an oppositely directed annular recess adapted for seating the body over a sectioned end of the bone; and
    a turn screw having a head accessible from said joint defining face and a shaft extending inwardly within the bone, a stem mounted to an end of said shaft and extending inwardly within a marrow filled interior of the bone, a plurality of outwardly displaceable branches hingedly supported to exterior locations of said stem and which are actuated by a like plurality of pivotal linkage mechanisms in response to rotation of said shaft, said branches pivoting outwardly and being adapted to engage inner surface locations associated with the bone and in order to engage the implant to the bone.

2. The implant as described in claim 1, further comprising a clip associated with each of said branches.

3. The implant as described in claim 1, further comprising said turn screw being recess mounted within said body in a direction facing said exposed joint defining face.

4. The implant as described in claim 1, further comprising a soft plastic lubricated surface applied to said exposed joint defining face.

5. The implant as described in claim 1, said implant further comprising a composite hard plastic material.

6. An artificial joint implant adapted for use with a bone, said implant comprising:
    a three dimensional shaped body having an exposed joint defining face;
    an oppositely directed annular recess adapted for seating the body over a sectioned end of the bone; and
    a turn screw accessible from said joint defining face and extending inwardly within the bone, said turn screw exhibiting threads for actuating at least one interior displaceable wing portion supported upon said threads and, in response to rotation of said screw, said wing portions being adapted to engage an inner surface associated with the bone to engage the implant to the bone.

7. The implant as described in claim 6, further comprising said turn screw being recess mounted within said body in a direction facing said exposed joint defining face.

8. The implant as described in claim 6, further comprising a soft plastic lubricated surface applied to said exposed joint defining face.

9. The implant as described in claim 6, said implant further comprising a composite hard plastic material.

10. An artificial joint implant adapted for use with a bone, said implant comprising:
    a three dimensional shaped body having an exposed joint defining face;
    an oppositely directed annular recess adapted for seating the body over a sectioned end of the bone;
    a stem extending from said body inwardly within the bone and exhibiting at least one support adapted to engage an inner bone surface and in order to engage the implant to the bone; and
    said stem further comprising a rotatable threaded shaft operable via an end face mounted turn screw for actuating said at least one support in an outward fashion, said support further comprising a rotatable wing nut portion.

\* \* \* \* \*